(12) United States Patent
Pilgrim et al.

(10) Patent No.: US 6,552,792 B1
(45) Date of Patent: Apr. 22, 2003

(54) WAVELENGTH MODULATED PHOTOACOUSTIC SPECTROMETER

(75) Inventors: Jeffrey S. Pilgrim, Santa Fe, NM (US); David S. Bomse, Santa Fe, NM (US)

(73) Assignee: Southwest Sciences Incorporated, Santa Fe, NM (US)

( * ) Notice: Subject to any disclaimer, the term of this patent is extended or adjusted under 35 U.S.C. 154(b) by 148 days.

(21) Appl. No.: 09/687,408

(22) Filed: Oct. 13, 2000

Related U.S. Application Data
(60) Provisional application No. 60/159,088, filed on Oct. 13, 1999.

(51) Int. Cl.[7] ............................................. G01N 21/61
(52) U.S. Cl. ...................................... 356/432; 356/432
(58) Field of Search ................................ 356/432, 437; 73/24.02

(56) References Cited

U.S. PATENT DOCUMENTS

| | | | | | |
|---|---|---|---|---|---|
| 4,051,371 A | * | 9/1977 | Dewey et al. | ............... | 250/343 |
| 4,255,971 A | * | 3/1981 | Rosencwaig | ................. | 73/606 |
| 5,913,234 A | * | 6/1999 | Julliard et al. | ............. | 73/24.02 |

OTHER PUBLICATIONS

Dewey, C.Forbes, Jr., "Octoacoustic Spectroscopy & Detection," Y–A Pao, editor, *Academic Press NY*, pp 62–67 (1977).

Feher, Miklos, et al., "Optoacoustic Trace–Gas Monitoring with Near–Infrared Diode Lasers," *Applied Optics*, vol. 33, No. 9, pp 1655–1658 (Mar. 20, 1994).

Iguchi, Toshio, "Modulation Waveforms for Second–Harmonic Detection with Tunable Diode Lasers," *Opt. Soc. Am. B*, vol. 3, No. 3, pp 419–423 (Mar. 1986).

Miklos, A., et al., "Experimental and Theoretical Invetigation of Phoacoustic–Signal Generation by Wavelength–Modulated Diode Laseres," *Apl. Phys. B*, vol. 58, pp 483–492 (1994).

Olsson, Bo E.R., et al., "Optoacoustic Lad–Salt Diode Laser Detection of Trace Species in a Flow System," *Applied Spectroscopy*, vol. 49, No. 8, pp 1103–1106 (1995).

White A.D., "Frequency Stavilization of Gas Lasers," *IEEE Journal of Quantum Electronics*, vol. QE–1, No. 8, pp 349–357 (1965).

\* cited by examiner

*Primary Examiner*—Richard A. Rosenberger
(74) *Attorney, Agent, or Firm*—Jeffrey D. Myers

(57) ABSTRACT

A wavelength modulated photoacoustic spectrometry system and method comprising: generating light from a light source; passing the light through a sample area; sampling sound produced by the light passing through the sample area with an acoustic detector; and controlling wavelength of the light with a wavelength controller, wherein the wavelength controller modulates the wavelength according to a waveform comprising square components.

28 Claims, 7 Drawing Sheets

WAVELENGTH MODULATED PHOTOACOUSTIC SPECTROMETER

CROSS-REFERENCE TO RELATED APPLICATIONS

This application claims the benefit of the filing of U.S. Provisional Patent Application Ser. No. 60/159,088, entitled "Wavelength Modulated Photoacoustic Spectrometer", filed on Oct. 13, 1999, and the specification thereof is incorporated herein by reference.

GOVERNMENT RIGHTS

The U.S. Government has a paid-up license in this invention and the right in limited circumstances to require the patent owner to license others on reasonable terms as provided for by the terms of Contract No. DMI-9860484 awarded by the National Science Foundation.

BACKGROUND OF THE INVENTION

1. Field of the Invention (Technical Field)

The present invention relates generally to the high-sensitivity detection of contaminants in gases by optical techniques generally termed photoacoustic and optoacoustic spectroscopy.

2. Background Art

Trace impurities in semiconductor process gases are among the most significant limits to product yield. Contaminants at the part-per-billion level can be problematic. In many cases, the unwanted compounds are ubiquitous in air—water vapor and oxygen are common examples—and can enter process tools along a variety of paths. Gas suppliers and end users face two problems, guaranteeing gas purity prior to shipment and maintaining purity during distribution within semiconductor fabrication facilities. Thus, there is a need for relatively inexpensive sensors for continuous, real time measurement of gas purity. Ideal sensors would be sufficiently cost effective that one could be installed in line at each process tool. The present invention's improvements to photoacoustic spectroscopy (PAS) and wavelength modulated photoacoustic spectroscopy (WM-PAS) provide these significant advantages for trace gas detection.

Optical spectroscopy is an effective, non-contact method for trace species detection and is well suited to continuous monitoring in process control systems. When wavelength-tunable diode lasers are used as light sources, their monochromatic output makes possible an exceptional combination of detection sensitivity and selectivity. Selectivity refers to the ability to detect the target species even in the presence of a huge excess of other compounds. Two types of techniques have been developed for achieving highly sensitive gas detection using linear optical absorption spectroscopy with diode lasers. In one case, wavelength modulation techniques (similar to frequency modulation) shift the detection bandwidth from DC, where the lasers are most noisy, to higher frequencies where laser excess noise (1/f noise) is unimportant. The other approach, called the noise canceler, uses a fast, simple transistor circuit to subtract the common mode noise in the measurements of the power exiting the laser and the power after the light beam has passed through the sample. When commercially available near-infrared diode lasers are used, both approaches have theoretical minimum detectable absorbances in the $10^{-8}$ range for a 1 Hz bandwidth. Here, absorbance is the fractional change in laser power due to molecular absorption. In practice, however, optical artifacts in the form of unwanted interference fringes (etalons) usually limit absorbance sensitivities to $\sim 1 \times 10^{-5}$.

Previous work by other researchers shows that absorbances in the $10^{-8}$ range and smaller can be detected using a simple, short ($\sim 10$ cm), single pass, optical cell using photoacoustic detection. Relatively inexpensive, compact instruments for continuous monitoring of trace impurities in semiconductor process gas are possible. An improvement to PAS, called wavelength modulated photoacoustic spectroscopy (WM-PAS), eliminates a major noise source associated with traditional implementations of PAS.

WM-PAS has been practiced in the prior art. An early description of the technique was provided by C. F. Dewey, Optoacoustic Spectroscopy and Detection (Y-H Pao, ed., Academic Press, New York, 1977), pp. 62–64. Others have since practiced the technique including M. Feher, et al., Applied Optics 33, 1655 (1994); A. Miklos, et al., Applied Physics B 58, 483 (1994); and B. E. R. Olsson, et al., Applied Spectroscopy 49, 1103 (1995). All use sinusoidal wavelength modulation waveforms and do not simultaneously provide for locking the optical source wavelength to the peak of the gaseous absorption feature as with the present invention.

To reiterate, photoacoustic spectroscopy is a well-known method pioneered by Bell for measuring weak optical absorbances indirectly. Optical absorption by the target compound heats the sample. The small temperature rise creates a change in pressure that is detected with a microphone. The magnitude of the pressure change depends in part on the product of the sample absorbance and the light source intensity. Usually, the light is chopped at an audio frequency, and the photoacoustic signal is detected using a lock-in amplifier synchronized to the chopping frequency. Photoacoustic detection is useful because modern microphones have low background noise and good linearity.

Wavelength modulated photoacoustic spectroscopy eliminates a major source of noise in photoacoustic spectroscopy and provides high sensitivity detection using modest power (few milliwatt) diode lasers. Also, the use of wavelength modulation with photoacoustic detection removes the main impediment to wavelength modulated optical absorption spectroscopy, optical interference fringes. The combined techniques provide a superior method for trace gas detection.

Photoacoustic measurements are often limited by noise due to weak absorption at the cell windows. This background signal is synchronous with the chopped or pulsed laser beam and can overwhelm signals due to absorbance by the target gas. Researchers have implemented a number of approaches to avoiding window noise, such as using acoustic baffles between the windows and the microphone or trying to time-resolve the "true" signal that originates closer to the microphone, but window effects remain a significant problem for photoacoustic detection.

WM-PAS avoids window noise by modulating the laser wavelength instead of the laser intensity. Optical absorption at the windows will still occur, but does not generate a synchronous, interfering signal. The basic principle of wavelength modulated photoacoustic detection is shown in FIG. 1. The laser wavelength is modulated sinusoidally across the absorption line. This wavelength modulation induces synchronous absorption which generates synchronous pressure waves at frequency f and its integer harmonics. FIG. 1 shows a photoacoustic wave whose primary frequency component is 2f. In this case, where the average (i.e., unmodulated wavelength) is coincident with the absorption line center, the 2f frequency component dominates because the laser wavelength samples the absorption line peak twice during each modulation period. These pressure waves—the photoacoustic signal—are detected using a microphone connected to a lock-in amplifier.

The laser wavelength is modulated by a small amount: only ~0.1 cm$^{-1}$ for a gas at atmospheric pressure. Absorption bands due to windows are orders of magnitude broader, so that the window absorption cross section is virtually constant across the wavelength modulation range. As a result, absorption due to the window does not introduce a synchronous acoustic signal. Wavelength modulation is ideally suited to diode lasers because laser wavelengths tune linearly with changing current. It is straightforward to add a small AC component to the laser drive current in order to effect the wavelength modulation.

The method of the present invention improves on traditional sinusoidal modulation of the wavelength in WM-PAS. It is known that the modified square wave (MSQ), FIG. 6b, modulation waveform can provide increased signal levels for 2f detection in wavelength modulated absorption experiments. T. Iguchi, Journal of the Optics Society of America B 3, 419 (1986). However, the MSQ waveform also amplifies etalon signal amplitudes in the same way as the gaseous absorption signal amplitude. Thus, in traditional WMS absorption experiments there is usually no advantage to the MSQ waveform. However, the limiting noise source in the WM-PAS technique is not usually etalons. Therefore, the MSQ waveform can provide increased PAS signals without concurrently increasing the limiting noise. The application of the MSQ to traditional WM-PAS is shown in FIG. 2. Raw photoacoustic signal is shown in FIG. 3, which has been obtained under identical conditions save for the type of wavelength modulation waveform. The MSQ waveform provides increased signal compared to the sinusoidal and triangle waveforms.

The present invention is also characterized by several additional advantages including:

Immunity to Etalons. Optical absorption spectroscopy including both wavelength modulation and noise canceler approaches are usually limited by unwanted optical interference fringes (etalons) instead of by fundamental noise sources such as laser shot noise. For commercial instruments, etalons typically constrain minimum detectable absorbances to ~10$^{-5}$, which is at least two orders of magnitude worse than is predicted from shot noise alone. Etalon effects can appear only as a small perturbation on the PAS signal and not as a false absorption signal (which is the case with direct absorption spectroscopy). This advantage is realized whether the wavelength modulation waveform is sinusoidal or the MSQ waveform. Thus, this etalon immunity is maintained with the higher performance MSQ waveform.

Line locking. The combination of wavelength modulation and photoacoustic detection according to the present invention also allows a method for stabilizing the laser wavelength to be coincident with the absorption line center.

SUMMARY OF THE INVENTION (DISCLOSURE OF THE INVENTION)

The present invention is of a wavelength modulated photoacoustic spectrometry system and method comprising: generating light from a light source; passing the light through a sample area; sampling sound produced by the light passing through the sample area with an acoustic detector; and controlling wavelength of the light with a wavelength controller, wherein the wavelength controller modulates the wavelength according to a waveform comprising square components. In the preferred embodiment, the wavelength controller additionally stabilizes the average wavelength to be coincident with an absorption line center. The waveform comprises alternating positive and negative squared peaks fluctuating about a center line, and preferably additionally comprises higher frequency and lower amplitude peaks between the squared peaks. The higher frequency and lower amplitude peaks preferably comprise a triangle waveform, a sine waveform, or a square waveform, have a frequency exceeding a frequency response of the acoustic detector, and have a frequency within the detection bandwidth of the acoustic detector with the wavelength controller employing feedback from the acoustic detector to stabilize the average wavelength to be coincident with an absorption line center. An optical detector may be employed to receive the light passed through the sample area, with its output being used by the wavelength controller to normalize the signal from the acoustic detector to light source power and/or to stabilize the average wavelength to be coincident with an absorption line center. The optical detector output is preferably demodulated at an odd harmonic of modulation frequency. A wavelength stepper may be employed with a data acquisition system for recording the demodulated signal from the acoustic detector at each wavelength step generated by the wavelength stepper. The stepping rate preferably allows at least three periods of the modulation frequency per step.

A primary advantage of the present invention is that it provides a minimum detectable concentration for moisture that is ten-fold better—for the same optical path length—than the sensitivity achieved using preexisting wavelength modulated optical absorption spectroscopy techniques.

Another advantage of the present invention is that it provides measurement linearity over three orders of magnitude.

An additional advantage of the present invention is that the novel wavelength modulation waveform increases WM-PAS detection sensitivity by more than a factor of two over sinusoidal waveforms.

Yet another advantage of the present invention is that it provides combined wavelength modulated optical absorption-based optical source wavelength stabilization (line locking) with WM-PAS detection.

Still another advantage of the present invention is that immunity to etalon fringes is maintained.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS

Figure 1:
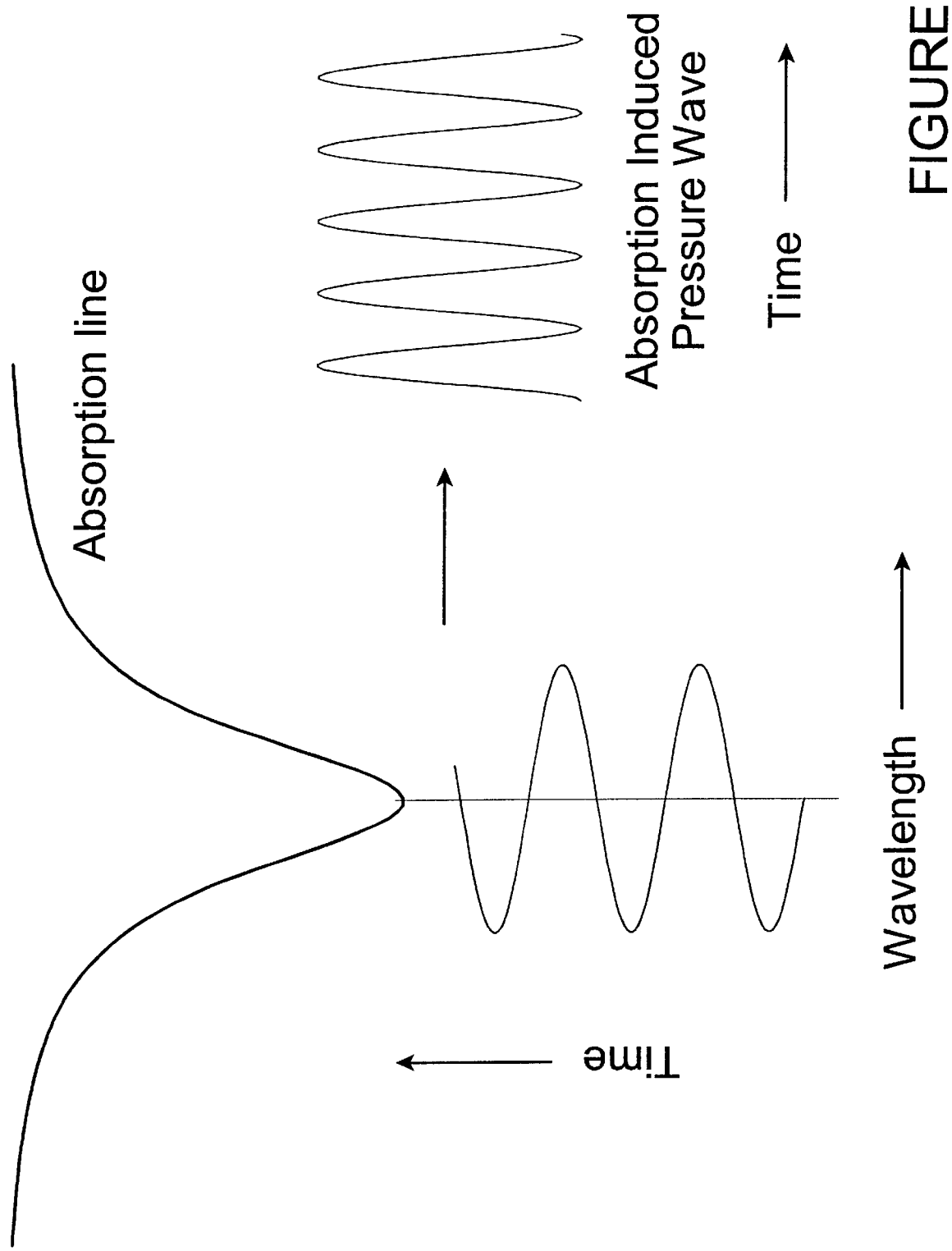
FIG. 1 (prior art) illustrates the principle of wavelength modulated photoacoustic spectroscopy. As the wavelength of an optical source is modulated by an amount comparable to the width of a gaseous absorption feature, differential absorption occurs leading to a synchronous heating of the irradiated sample which, in turn, leads to a synchronous pressure wave having frequency components including harmonics of the modulation frequency.

Best Modes for Carrying out the Invention

The present invention provides a method for quantitatively detecting the specific concentration of a gaseous species in a gas sample employing a wavelength modulated photoacoustic spectrometer. The method preferably comprises: (a) providing an optical source whose wavelength can be tuned over an absorption feature of the target gas and whose wavelength can be modulated in an arbitrarily defined fashion; (b) situating the gaseous sample such that the optical source beam traverses the sample and situating an acoustic detector so as to detect the presence of photoacoustic signal; and (c) situating an optical detector such that the optical source beam, after traversing the sample, impinges upon the detector, the detector being used for purposes of locking the optical source wavelength onto the peak of the gaseous absorption feature and for optical source power normalization.

The invention also provides a gas detection system for quantitatively detecting the specific concentration of a gaseous species in a gas sample is provided wherein the gaseous sample absorbs light emitted by the modulated optical source thereby producing a photoacoustic signal, the optical source being modulated in wavelength in a manner so as to maximize the produced photoacoustic signal. The gas detection system preferably comprises: (a) an optical source, preferably a laser, with an operating wavelength coincident or near-coincident with an absorption feature of the target gaseous species, the optical source being capable of tuning in wavelength over the absorption feature of the target gaseous species in a particular fashion specified by the operator; (b) a container for containing the gas sample so that the optical source beam traverses the sample, the container providing access for photoacoustic signal measurement by an acoustic detector; and (c) an optical detector for collecting the optical source beam containing information on the gaseous absorption feature for purposes of locking the optical source wavelength onto the peak of the gaseous absorption feature and for normalizing the photoacoustic signal to optical source power.

The present invention provides a commercially-viable photoacoustic-based trace gas sensor with superior sensitivity over systems using sinusoidal wavelength modulation waveforms. Additionally, source wavelength-locked operation provides for a sensor that can run unattended for extended periods while maintaining superior sensitivity.

The invention improves upon wavelength modulated photoacoustic spectroscopy by including methods for light source wavelength stabilization (line locking) and by increasing detection sensitivity through the use of non-sinusoidal wavelength modulation waveforms. Wavelength stabilization is important for applications that benefit from continuous monitoring of a target species.

The invention uses a wavelength tunable light source such as a diode laser. The wavelength of the light source is modulated at a selected frequency f where the extent (depth) of modulation is chosen to be comparable to the width of an absorption feature of interest. Light from the source is directed through a sample that is also in contact with a microphone. When the average (unmodulated) wavelength of the light source is coincident or nearly coincident with the center of the absorption feature of the target species, one obtains a signal that can be related to the sample absorbance (and, hence, to the concentration of the absorbing species) by measuring the magnitude of the microphone output occurring at the modulation frequency, f, or at an integral harmonic of the modulation frequency, nf, where n=2, 3, 4, etc. Detection at the modulation frequency, f, can also be generalized as detection at nf for n=1. The signal is recovered by processing the microphone output with a phase sensitive detector such as a lock-in amplifier or mixer where the reference waveform (local oscillator) is derived from the modulation waveform.

Figure 2:
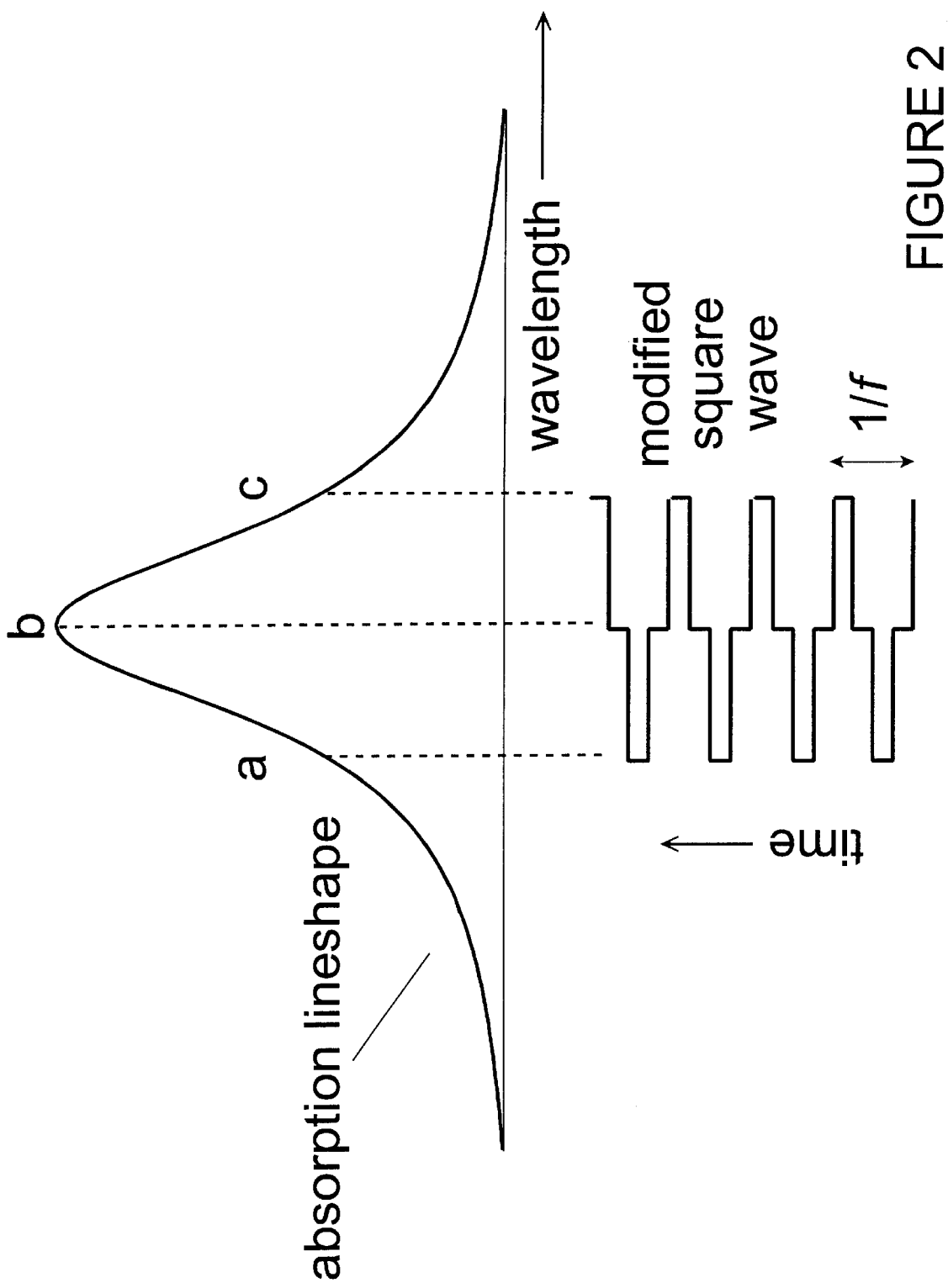
FIG. 2 illustrates the method of the present invention for improvement of wavelength modulated photoacoustic spectroscopy. The implementation of a modified square wave for wavelength modulation increases the signal amplitude due to the greater fraction of a modulation period spent on the peak of the absorption feature. Signals are amplified by this approach without incurring an increase in "noise" as would be the case in an etalon-limited wavelength modulated absorption-based technique.
Figure 4:
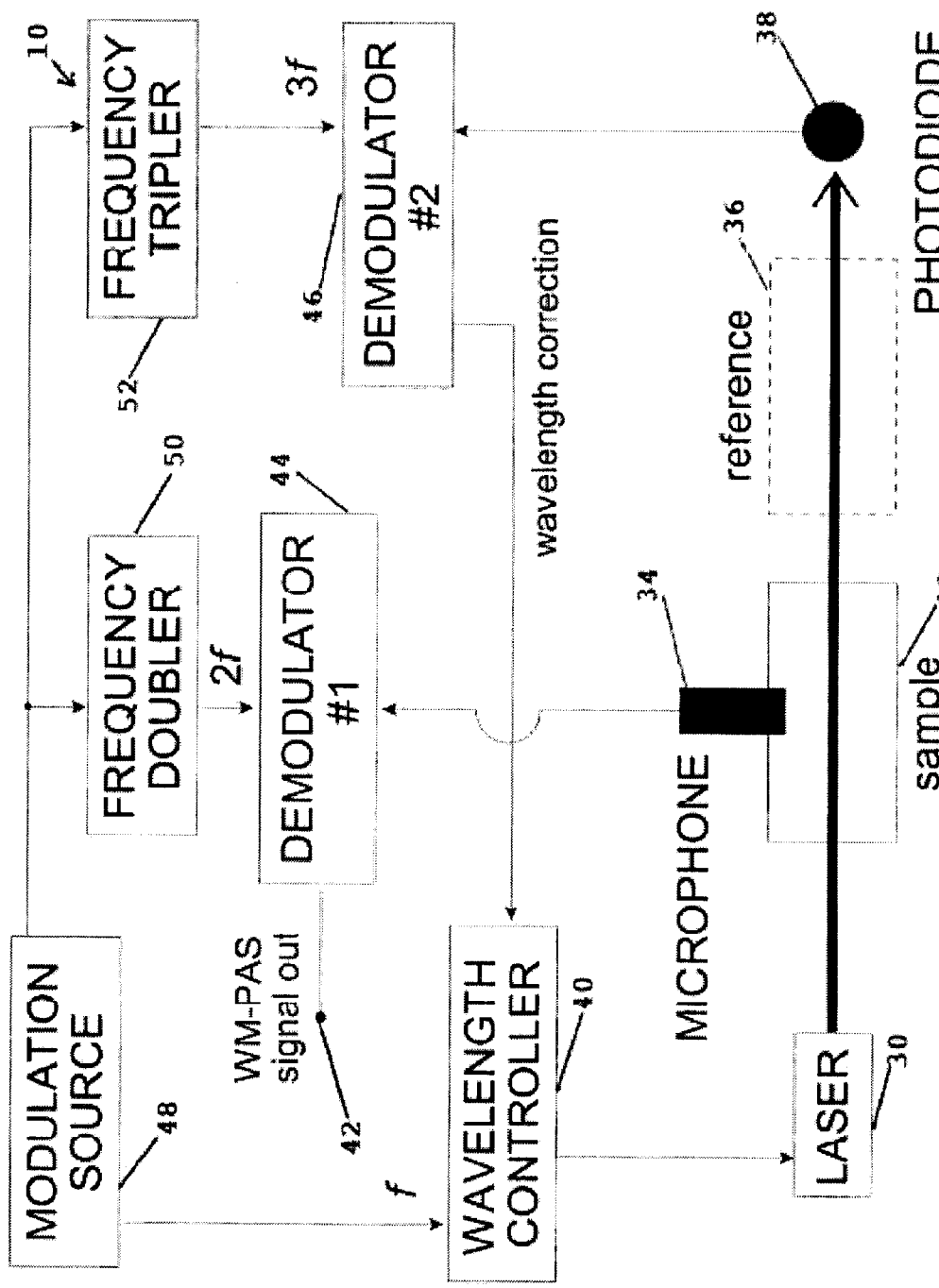
FIG. 4 is a schematic diagram of a first embodiment of the system of the present invention.

A first system embodiment 10 is shown schematically in FIG. 4. The wavelength of a diode laser 30 is modulated 48 at frequency f by adding 40 a MSQ component to the laser drive current. The MSQ frequency is defined in FIG. 2 as the inverse of the waveform period. Light from the laser passes through a cell 32 that is equipped with a microphone 34, then through a reference cell 36, shown in phantom, containing an amount of the target species, and finally impinges on a photodiode detector 38. The microphone signal is demodulated 44 at frequency 2f 50 while the average laser wavelength is constrained 46 to coincide with the center of the absorption line of interest. The photoacoustic 2f signal is a maximum at this wavelength and the magnitude of the signal can be used for continuous monitoring of the concentration of the target species. It will be appreciated that demodulation 44 at other harmonics may be used for obtaining WM-PAS signal 42. Additionally, multiple harmonics may be obtained simultaneously to provide multiple-independent measurements of PAS signal.

The average laser wavelength is constrained to the center of the absorption line using the photodiode to monitor the wavelength modulated absorption signal due to the target gas within a reference optical path. This wavelength control method, called line-locking, is well known, A. D. White, "Frequency Stabilization of Gas Lasers," IEEE Journal of Quantum Electronics QE-1, 349–357 (1965), and is particularly well-suited to the present invention because the wavelength modulation used in the present invention for improved photoacoustic detection can also be used, without modification, to implement line-locking. In the first embodiment, the output from the photodiode detector 38 is demodulated 46 at frequency 3f 52 to produce a signal that is nominally zero when the average laser wavelength is coincident with the center of the absorption line and varies linearly with small displacements of the wavelength away from line center. This 3f signal is used as part of a feedback loop to control the laser average wavelength to the absorption line center. It will be appreciated that other odd harmonics of the modulation frequency may be used for implementing line-locking. Additionally, in the event that WM-PAS signal is always present in the sample cell, an odd harmonic of the modulation frequency as measured by the microphone may be used to implement line-locking. This variation is, of course, not practical in an instrument where the concentration of the gaseous target species may go below that required to achieve sufficient stability in the wavelength of the optical source on the gaseous absorption feature.

Figure 5:
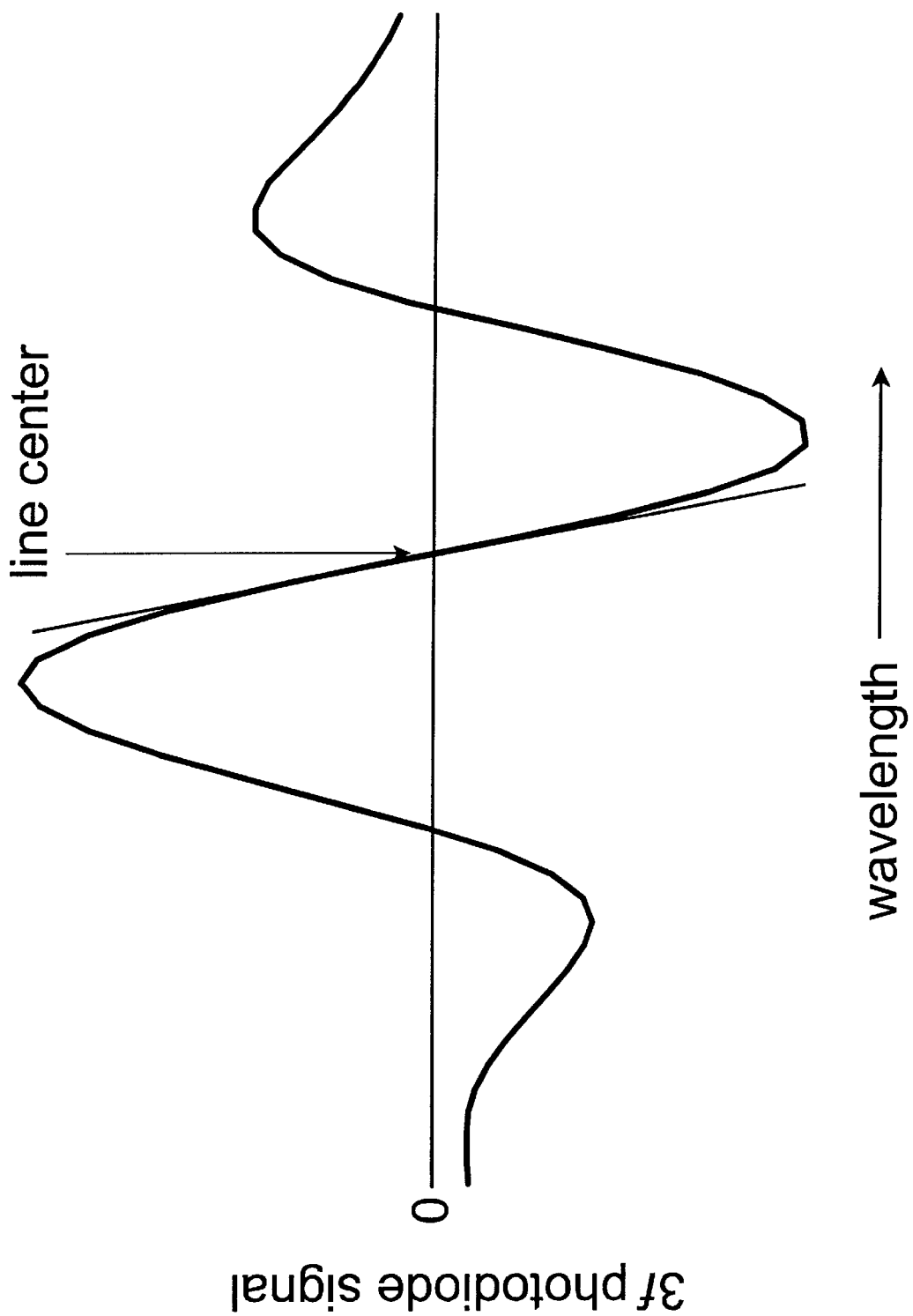
FIG. 5 is an experimentally obtained 3f absorption spectrum used for laser wavelength stabilization (line locking) in the first embodiment.

Any odd harmonic (i.e., nf for odd values of n) demodulated signal from the photodiode detector can be used for line-locking. The 3f signal is used instead of the 1f signal in this embodiment because the 1f signal also includes an offset due to the synchronous changes in diode laser output power with varying injection current. FIG. 5 shows a representative 3f spectrum of an absorption line due to water vapor. The zero crossing at line center is identified in the figure, as is the nearly linear response in signal to changing wavelength near the zero crossing.

The wavelength modulated photoacoustic signal strength is proportional to the laser intensity. Thus, an additional advantage of the photodiode is that the magnitude of its output can be used to correct the photoacoustic signal for variations in laser power.

Key advantages of the first embodiment are due to the high sensitivity possible from wavelength modulated photoacoustic spectroscopy using the MSQ waveform combined with the large duty cycle and rapid time response inherent from a line-locked spectroscopic measurement. Specifically, wavelength modulation reduces the size of the background photoacoustic signal arising from broad band absorption by the windows that is present even in the absence of the target gas. In traditional photoacoustic measurements, this background appears as an offset on the "true" signal and can reduce the accuracy of species concentration measurements. The present invention, by minimizing such unwanted offsets, improves the usefulness of measurements made at a single, nominal wavelength.

A variation of the first embodiment is useful for measurement of species present in the ambient path external to the sample cell that present a suitable signal for line locking. This case eliminates the need for a reference cell shown in phantom in FIG. 4. Line locking is performed using the optical absorbance due to the ambient concentration of the target gas. The photoacoustic cell is mechanically isolated from the ambient atmosphere; therefore, absorbance by the target gas in the optical path external to the cell does not contribute to the photoacoustic signal observed by the microphone within the cell.

Figure 3:
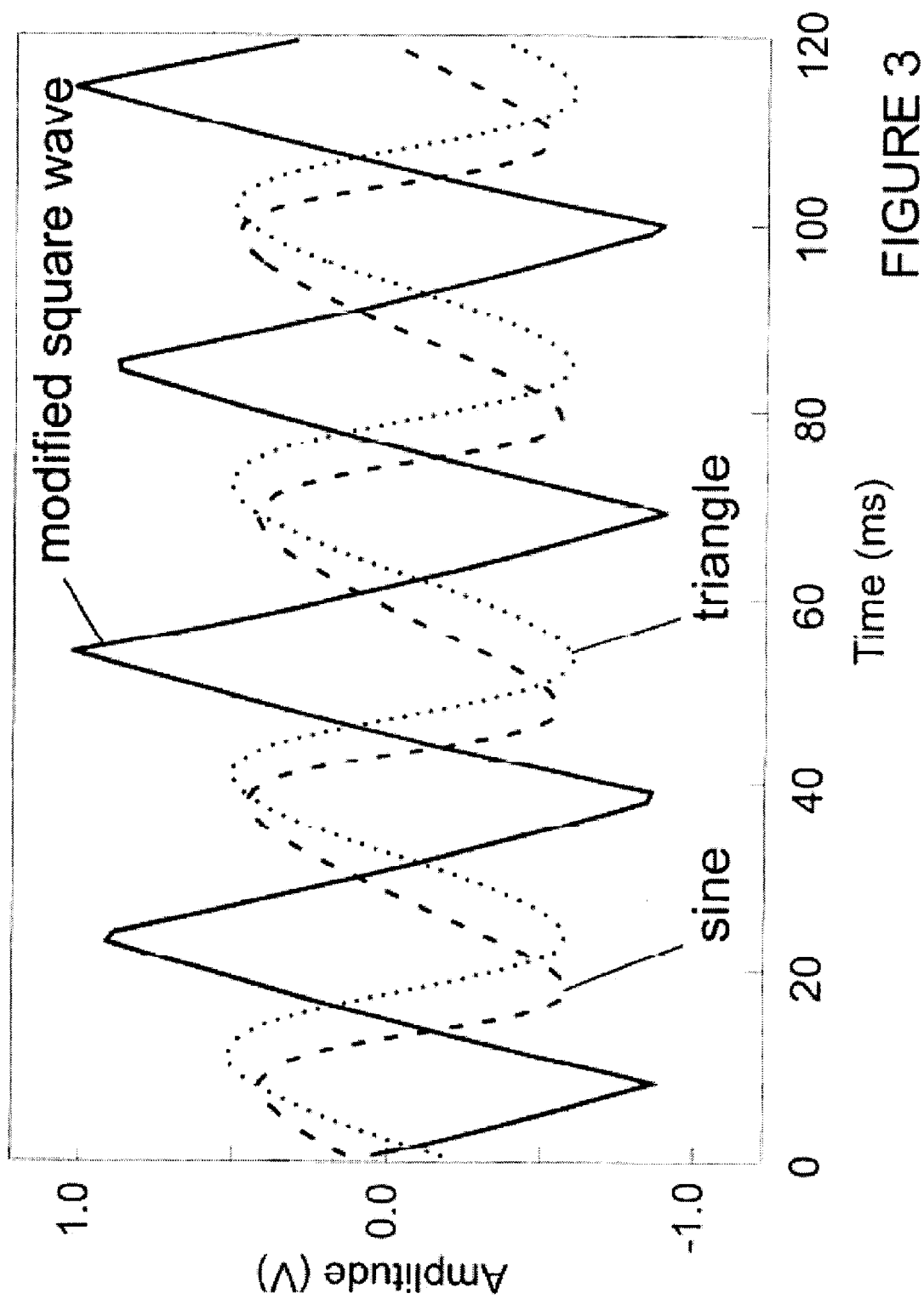
FIG. 3 presents a comparison of raw photoacoustic signal in the time domain obtained using several modulation waveforms. The modified square wave provides a quite superior signal to that of the prior art sine wave modulation waveform.
Figure 6:
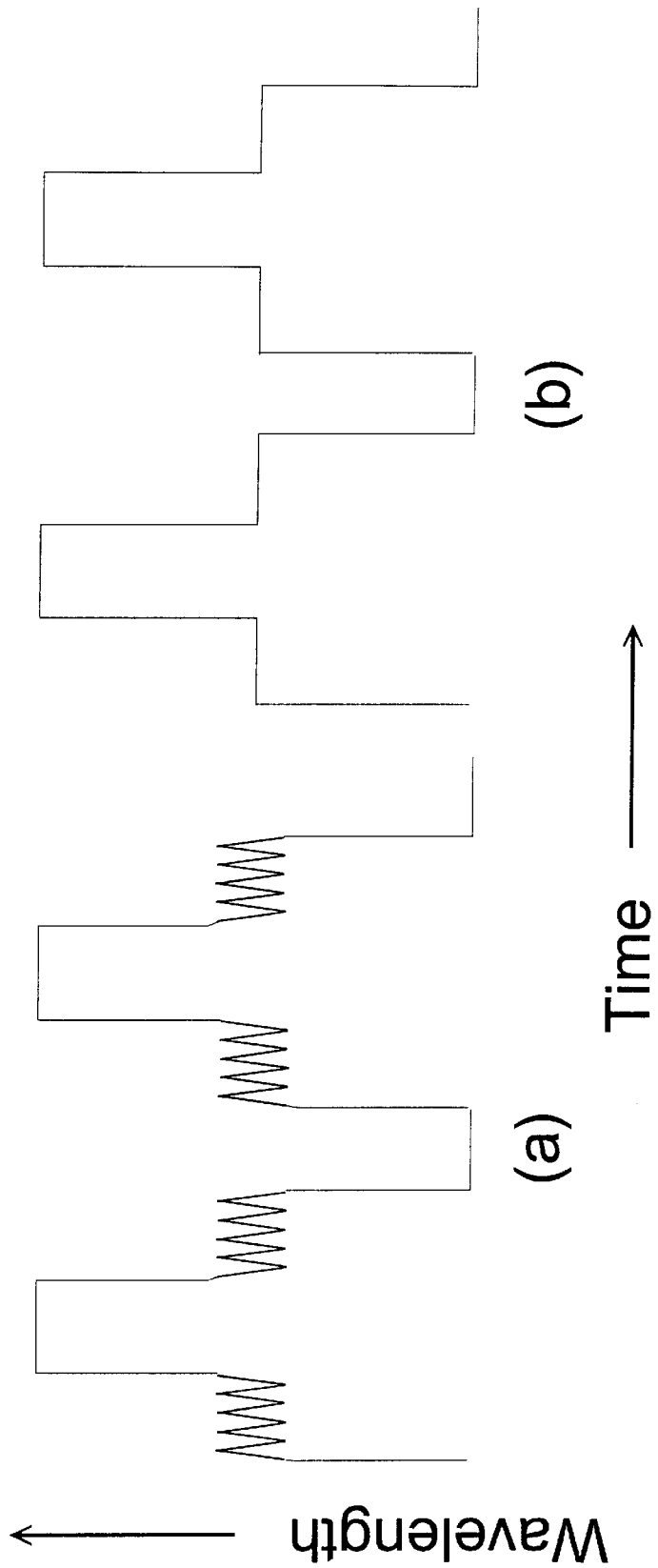
FIG. 6a shows a novel modulation waveform designed to increase wavelength modulated photoacoustic spectroscopy sensitivity while simultaneously providing improved line-locking capability over the simple modified square wave.
FIG. 6b (prior art) shows the simple modified square waveform (MSQ) as described by Iguchi for improving 2f signal in absorption spectroscopy.

An additional variation of the first embodiment uses a novel wavelength modulation waveform shown in FIG. 6a. Wavelength modulation using the modified square wave provides larger wavelength modulated photoacoustic signals than does modulation with a sine wave or a triangle wave (FIG. 3). Iguchi's modified square wave is shown in FIG. 6b. The modified square wave is less useful for line locking, however, as it suppresses odd-harmonic sensitivity. In fact the MSQ waveform only amplifies harmonics of the modulation frequency, f, that correspond to (4n+2)f where n are positive integers. The novel waveform shown in FIG. 6a maintains the signal enhancement obtained from the simple modified square wave while also imposing a small amplitude, high frequency component suitable for line locking. The high frequency component is selected to exceed the frequency response of the microphone—avoiding unwanted microphone signals—and is applied only to a selected portion of the total waveform. When the laser wavelength is coincident with the center of the absorption feature the high frequency modulation samples only the line center which is the region most useful for line locking. The high frequency component can be any waveform suitable for line locking; sine waves and triangle waves are the most easily implemented, while square waves would provide the highest sensitivity to absorption line center deviations.

Figure 7:
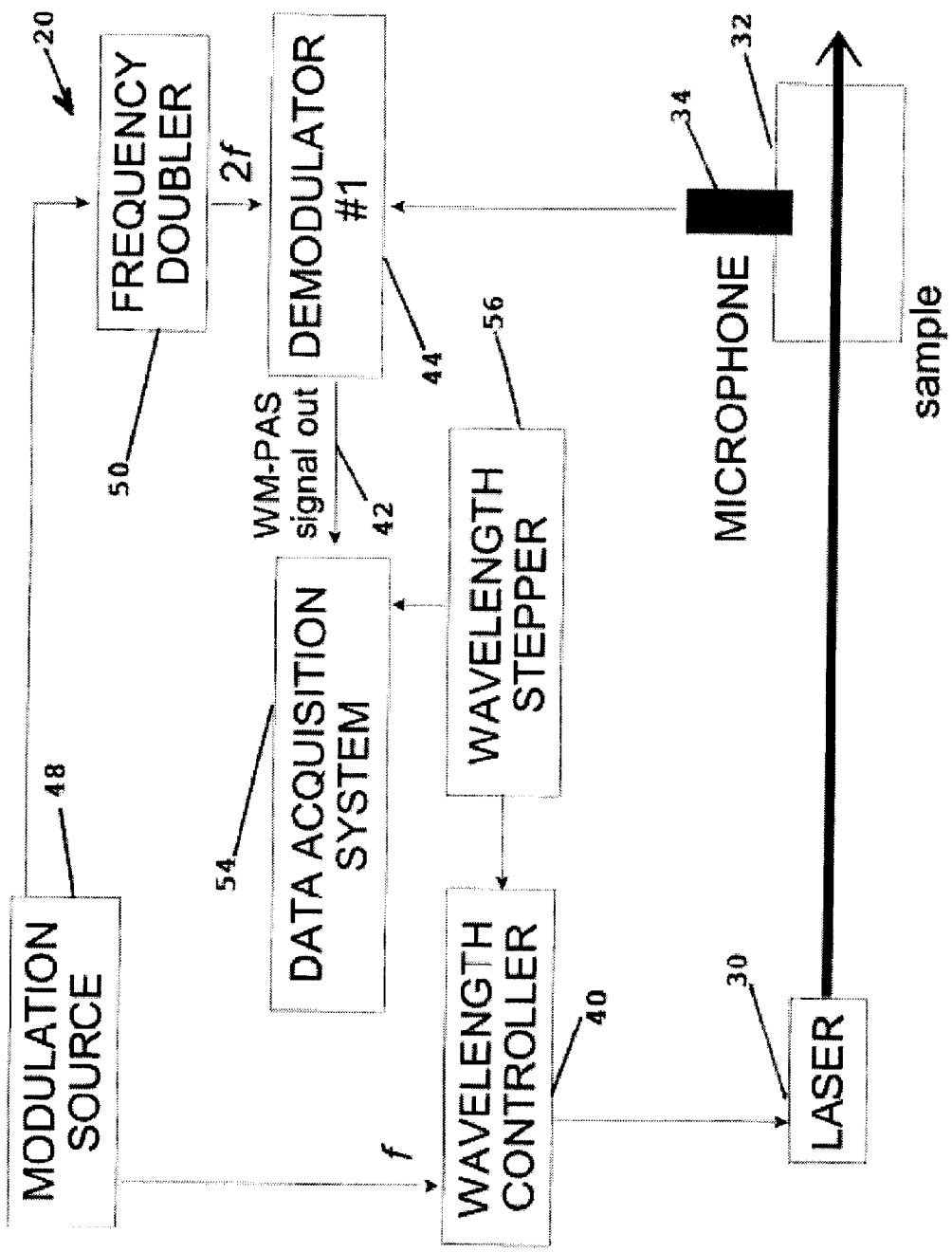
FIG. 7 is a schematic diagram of a second embodiment of the system of the present invention.

The second embodiment of the system 20 of the invention, shown schematically in FIG. 7, allows acquisition of wavelength modulated photoacoustic spectra. The average laser wavelength is stepped 56 across the target species absorption feature and the demodulated microphone signal is recorded by a data acquisition system 54 at each wavelength step. The wavelength stepping rate is slow compared with the modulation frequency, preferably allowing at least three periods of the modulation frequency per step. This embodiment is useful when background acoustic noise at the demodulation frequency may interfere with the photoacoustic measurement or when information is required from more than one absorption feature. In this embodiment, the simple MSQ waveform is sufficient for wavelength modulation. This embodiment is also useful for detection of multiple trace gaseous species.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A wavelength modulated photoacoustic spectrometry system comprising:
    a light source;
    a sample area receiving light from said light source;
    an acoustic detector proximate said sample area;
    a wavelength controller controlling wavelength of light emitted by said light source, wherein said wavelength controller modulates the wavelength according to a waveform comprising square components.

2. The system of claim 1 wherein said wavelength controller additionally stabilizes average wavelength to be coincident with an absorption line center.

3. The system of claim 1 wherein said waveform comprises alternating positive and negative squared peaks fluctuating about a center line.

4. The system of claim 3 wherein said waveform additionally comprises higher frequency and lower amplitude peaks between said squared peaks.

5. The system of claim 4 wherein said higher frequency and lower amplitude peaks comprise a waveform selected from the group consisting of triangle waveforms, sine waveforms, and square waveforms.

6. The system of claim 4 wherein said higher frequency and lower amplitude peaks has a frequency exceeding a frequency response of said acoustic detector.

7. The system of claim 4 wherein said higher frequency and lower amplitude peaks has a frequency within a detection bandwidth of said acoustic detector and wherein said wavelength controller employs feedback from said acoustic detector to stabilize average wavelength to be coincident with an absorption line center.

8. The system of claim 1 additionally comprising an optical detector receiving the light passed through said sample area.

9. The system of claim 8 wherein said optical detector generates output used by said wavelength controller to normalize a signal from said acoustic detector to light source power.

10. The system of claim 8 wherein said optical detector generates output used by said wavelength controller to stabilize average wavelength to be coincident with an absorption line center.

11. The system of claim 10 wherein said output is demodulated at an odd harmonic of modulation frequency.

12. The system of claim 1 wherein said wavelength controller comprises a wavelength stepper.

13. The system of claim 12 additionally comprising a data acquisition system for recording a demodulated signal from said acoustic detector at each wavelength step generated by said wavelength stepper.

14. The system of claim 12 wherein a stepping rate of said wavelength stepper allows at least three periods of the modulation frequency per step.

15. A wavelength modulated photoacoustic spectrometry method comprising the steps of:
    a) generating light from a light source;
    b) passing the light through a sample area;
    c) sampling sound produced by the light passing through the sample area with an acoustic detector;
    d) controlling wavelength of the light with a wavelength controller, wherein the wavelength controller modulates the wavelength according to a waveform comprising square components.

16. The method of claim 15 wherein in the controlling step the wavelength controller additionally stabilizes average wavelength to be coincident with an absorption line center.

17. The method of claim 15 wherein in the controlling step the waveform comprises alternating positive and negative squared peaks fluctuating about a center line.

18. The method of claim 17 wherein in the controlling step the waveform additionally comprises higher frequency and lower amplitude peaks between the squared peaks.

19. The method of claim 18 wherein in the controlling step the higher frequency and lower amplitude peaks comprise a waveform selected from the group consisting of triangle waveforms, sine waveforms, and square waveforms.

20. The method of claim 18 wherein in the controlling step the higher frequency and lower amplitude peaks has a frequency exceeding a frequency response of the acoustic detector.

21. The method of claim 18 wherein in the controlling step the higher frequency and lower amplitude peaks has a frequency within a detection bandwidth of the acoustic detector and wherein the wavelength controller employs feedback from the acoustic detector to stabilize average wavelength to be coincident with an absorption line center.

22. The method of claim 15 additionally comprising the step of receiving with an optical detector the light passed through the sample area.

23. The method of claim 22 additionally comprising the step of producing with the optical detector output used by the wavelength controller to normalize a signal from the acoustic detector to light source power.

24. The method of claim 22 additionally comprising the step of producing with the optical detector output used by the wavelength controller to stabilize average wavelength to be coincident with an absorption line center.

25. The method of claim 24 additionally comprising the step of demodulating the output at an odd harmonic of modulation frequency.

26. The method of claim 15 wherein the controlling step comprises the step of employing a wavelength stepper.

27. The method of claim 26 additionally comprising the step of recording with a data acquisition system a demodulated signal from the acoustic detector at each wavelength step generated by the wavelength stepper.

28. The method of claim 26 wherein in the employing step a stepping rate of the wavelength stepper allows at least three periods of the modulation frequency per step.

\* \* \* \* \*